(12) United States Patent
Imaizumi et al.

(10) Patent No.: US 7,670,286 B2
(45) Date of Patent: Mar. 2, 2010

(54) ELECTRONIC ENDOSCOPIC DEVICE HAVING A COLOR BALANCE ADJUSTMENT SYSTEM

(75) Inventors: Katsuichi Imaizumi, Hachioji (JP); Isami Hirao, Hachioji (JP); Yoshinori Takahashi, Hachioji (JP); Takeshi Ozawa, Sagamihara (JP); Nobuyuki Doguchi, Hino (JP); Sakae Takehana, Sagamihara (JP)

(73) Assignee: Olympus Corporation, Tokyo (JP)

( * ) Notice: Subject to any disclaimer, the term of this patent is extended or adjusted under 35 U.S.C. 154(b) by 682 days.

(21) Appl. No.: 10/869,239

(22) Filed: Jun. 16, 2004

(65) Prior Publication Data

US 2004/0267091 A1 Dec. 30, 2004

(30) Foreign Application Priority Data

Jun. 17, 2003 (JP) .............................. 2003-172458

(51) Int. Cl.
*A61B 1/06* (2006.01)

(52) U.S. Cl. .......................... 600/160; 348/70; 600/109
(58) Field of Classification Search ................. 600/118, 600/160, 178, 180; 348/68–70
See application file for complete search history.

(56) References Cited

U.S. PATENT DOCUMENTS

| | | | |
|---|---|---|---|
| 5,278,642 A | | 1/1994 | Danna et al. |
| 6,293,911 B1 * | | 9/2001 | Imaizumi et al. ............ 600/160 |
| 6,464,633 B1 * | | 10/2002 | Hosoda et al. .............. 600/178 |
| 6,635,011 B1 * | | 10/2003 | Ozawa et al. ................ 600/178 |
| 6,652,451 B2 * | | 11/2003 | Murata et al. ................ 600/118 |
| 6,902,527 B1 * | | 6/2005 | Doguchi et al. ............. 600/109 |
| 2002/0177751 A1 * | | 11/2002 | Ueno et al. .................. 600/160 |
| 2003/0050532 A1 * | | 3/2003 | Doguchi ...................... 600/109 |
| 2003/0060683 A1 * | | 3/2003 | Abe et al. .................... 600/180 |
| 2003/0176768 A1 * | | 9/2003 | Gono et al. .................. 600/109 |

FOREIGN PATENT DOCUMENTS

| | | |
|---|---|---|
| JP | 2002-95635 | 4/2002 |
| JP | 2002-336196 | 11/2002 |
| WO | WO 94/18801 | 8/1994 |

* cited by examiner

*Primary Examiner*—John P Leubecker
*Assistant Examiner*—Philip R Smith
(74) *Attorney, Agent, or Firm*—Scully, Scott, Murphy & Presser, P.C.

(57) ABSTRACT

The electronic endoscope device in accordance with the present invention comprises an image pick-up unit capable of acquiring an object image with respect to illumination light employed for illuminating the object for each prescribed wavelength band, an exposure period setting circuit for setting the exposure period of the image pick-up unit corresponding to the each wavelength band, an amplification circuit for amplifying picked-up image signals of the object image obtained with the image pick-up unit corresponding to the each wavelength band, and a control circuit for controlling the amplification circuit such that the picked-up image signals corresponded to the each wavelength band of the object image that are acquired with the image pick-up unit at the exposure period set corresponding to the each wavelength band set by the exposure period setting circuit are amplified at amplification factors computed corresponding to the exposure period that is set corresponding to the each wavelength band.

56 Claims, 9 Drawing Sheets

ELECTRONIC ENDOSCOPIC DEVICE HAVING A COLOR BALANCE ADJUSTMENT SYSTEM

CROSS-REFERENCE TO RELATED APPLICATION

This application claims benefits of Japanese Application No. 2003-172458 filed in Japan on Jun. 17, 2003, the contents of which are incorporated by this reference.

BACKGROUND OF THE INVENTION

1. Field of the Invention

The present invention relates to an electronic endoscope device for obtaining images with an image pick-up element which captures an object image by accumulating an electric charge, and to a signal processing unit used in this electronic endoscope device.

2. Related Art Statement

Electronic endoscope devices have been widely used for observing the digestion tract, for example, esophagus, stomach, small intestines, and large intestines, or bronchial tube such as lungs by inserting an endoscope into a body cavity, and, if necessary, conducting a variety of medical treatments by using therapeutic instruments inserted into the dedicated channels.

Electronic endoscope devices of a field sequential system are known as electronic endoscopes in which a rotary optical filter is provided in a light source unit, the object is sequentially illuminated with red, green, and blue light from this light source unit, the light thus obtained from the object is received by monochromatic image pick-up elements, signal processing is conducted in a signal processing unit, and the color image obtained is outputted to a display unit. Because of differences in wavelength characteristics of optical filters or spectral sensitivity characteristics of the image pick-up elements among the electronic endoscope devices of a field sequential system, adjustment of white balance has been conducted by using electronic circuits in typical electronic endoscope devices.

The white balance adjustment is conducted by pushing down a white-balance setting switch in a state that the image of a white body has been picked up. When the switch is pushed down, the white balance adjustment circuit adjusts the color balance such that the ratio of the amplitudes of the B signal and R signal to the G signal comes to a prescribed value. In case of analog circuitry, this adjustment typically involves comparing the outputs of all the signals by a comparator and adjusting little by little the amplification factors so as to obtain convergence to the prescribed color. However, in this case, a large number of frame images are required before the correct white color adjustment is completed and, therefore, the adjustment is a time-consuming procedure.

On the other hand, the adjustment of color balance with digital circuitry is most often conducted by sampling signals of each color within one frame, directly computing the amplification factors of B signal or R signal with a CPU or the like from the intensity ratio thereof, and amplifying each signal by using a digital multiplier. In this case, the adjustment of white balance does not take a long time.

Further, diagnostics employing electronic endoscope devices has recently begun involving auto-fluorescence observations using auto-fluorescence of living-body tissue, in addition to normal observations in which color images similar to those observed by the naked eye are displayed on a monitor.

In the auto-fluorescence observations, diagnostics is conducted according to the fact that spectra of auto-fluorescence emitted from the living-body tissue when it is illuminated with excitation light within a UV to blue range is different between the normal mucous membrane and a tumor. In this case, a lesion portion can be clearly recognized by displaying the image of auto-fluorescence into the reflected light image returned due to reflection from the living-body tissue on a display, the reflected light image having allocation of respective different colors. At this time, the wavelength of the light illuminated is restricted by using narrow-band optical filters (see, for example, Japanese Patent Application Laid-open No. 2002-95635) such that the spectral distribution in each wavelength band becomes discreet.

Furthermore, in the conventional electronic endoscope devices, the adjustment of color balance is typically conducted by employing a white object as a reference (see, for example, Japanese Patent Application Laid-open No. 2002-336196), but there are also electronic endoscope devices in which lesion portions in any patient can be observed with a fixed color tone by adjusting the color balance by employing the color of the normal mucous membrane of the patient as a reference during auto-fluorescence observations.

In such conventional electronic endoscope devices, the amplification factor of the amplifier of the signal processing unit has been adjusted for each color (each wavelength band) to adjust the color balance. For this reason, a small difference in the amplification factors between the colors has not caused significant problems, but when the difference in the amplification factors between the colors is large, noise is often increased by a color component of the image with a high amplification factor.

In particular, in electronic endoscope devices for fluorescent observations, the difference in brightness of the fluorescence emitted by mucous membranes of the patients is large among the patients, and the difference in amplification factors between the colors has to be increased to correct the aforementioned difference in brightness which could result in images with a high noise level.

Furthermore, because fluorescence is extremely weak, the quantity of illumination light for obtaining a reflected light image has to be made lower than the quantity of illumination of excitation light. For this purpose, the transmission wavelength band of the filter is narrowed or transmissivity thereof is decreased. This could easily lead to a wavelength error during optical filter manufacture and produce a relatively large negative effect on the image color. For example, in case of a 10 nm error in a filter with a transmission band with a half-width of 100 nm, the error of the transmitted light intensity is about 10%, but in case of a 10 nm error in a filter with a transmission band with a half-width of 20 nm, the error of the transmitted light intensity is about 50%. As a result, the difference in amplification factors between the colors easily became large during color balance adjustment and the probability of obtaining images with a high level of noise is large.

Furthermore, in case of endoscope devices equipped with electronic shutters, color correction can be also conducted by controlling the exposure period. However, in endoscope devices requiring light shielding with a rotary filter plate or the like, the exposure period that is electrically set and the exposure quantity falling upon the image pick-up element do not show a simple linear relationship. This is because the luminous flux crossing the rotary filter is not perfectly converged in one spot but has a certain surface area.

FIG. 11 is a graph illustrating the relationship between the exposure quantity (in case no electronic shutter is used) and time with respect to such a rotary filter. FIG. 12 is a graph illustrating the relationship between the exposure quantity and exposure period with respect to the rotary filter.

The ideal relationship between the exposure quantity and time obtained when one filter in the rotary filter is inserted in the luminous flux is represented by a broken line 91 shown in FIG. 11, but actual relationship is represented by a solid line 92 shown in FIG. 11.

Furthermore, referring to FIG. 11, if an assumption is made that an electronic shutter is used and the electric charge sweep is carried out at the point A of time and that the exposure period is ended at the point B of time, then the exposure period will be the A-B period in FIG. 11. The relationship between the exposure period and exposure quantity at this time is shown in FIG. 12. Referring to FIG. 12, ideally speaking, the exposure period and exposure quantity are preferably proportional to each other, as shown by a broken line 93, but in reality they show a complex relationship represented by a solid line 94. Furthermore, the characteristics of the solid line 92 shown in FIG. 11 or solid line 94 shown in FIG. 12 differ depending on the type or individual features of the endoscope or light source unit. For this reason, in the electronic endoscope devices using rotary filter, a strict color balance has been difficult to set only by simple adjustment of exposure period.

BRIEF SUMMARY OF THE INVENTION

Briefly speaking, the electronic endoscope device in accordance with the present invention comprises an image pick-up unit capable of acquiring an object image with respect to illumination light employed for illuminating the object for each prescribed wavelength band, an exposure period setting circuit for setting the exposure period of the image pick-up unit corresponding to the each wavelength band, an amplification circuit for amplifying picked-up image signals of the object image obtained with the image pick-up unit corresponding to the each wavelength band, and a control circuit for controlling the amplification circuit such that the picked-up image signals corresponding to the each wavelength band of the object image acquired with the image pick-up unit at the exposure period set corresponding to the each wavelength band set by the exposure period setting circuit are amplified at amplification factors that are computed corresponding to the exposure period that is set corresponding to the each wavelength band.

Additional features and advantages of the invention will be set forth in the description which follows, and in part will be obvious from the description, or may be learned by practice of the invention. The features and advantages of the invention may be realized and obtained by means of the instrumentalities and combinations particularly pointed out hereinafter.

DETAILED DESCRIPTION OF THE PREFERRED EMBODIMENTS

The preferred embodiments of the present invention will be described below with reference to the appended drawings.

Figure 1:
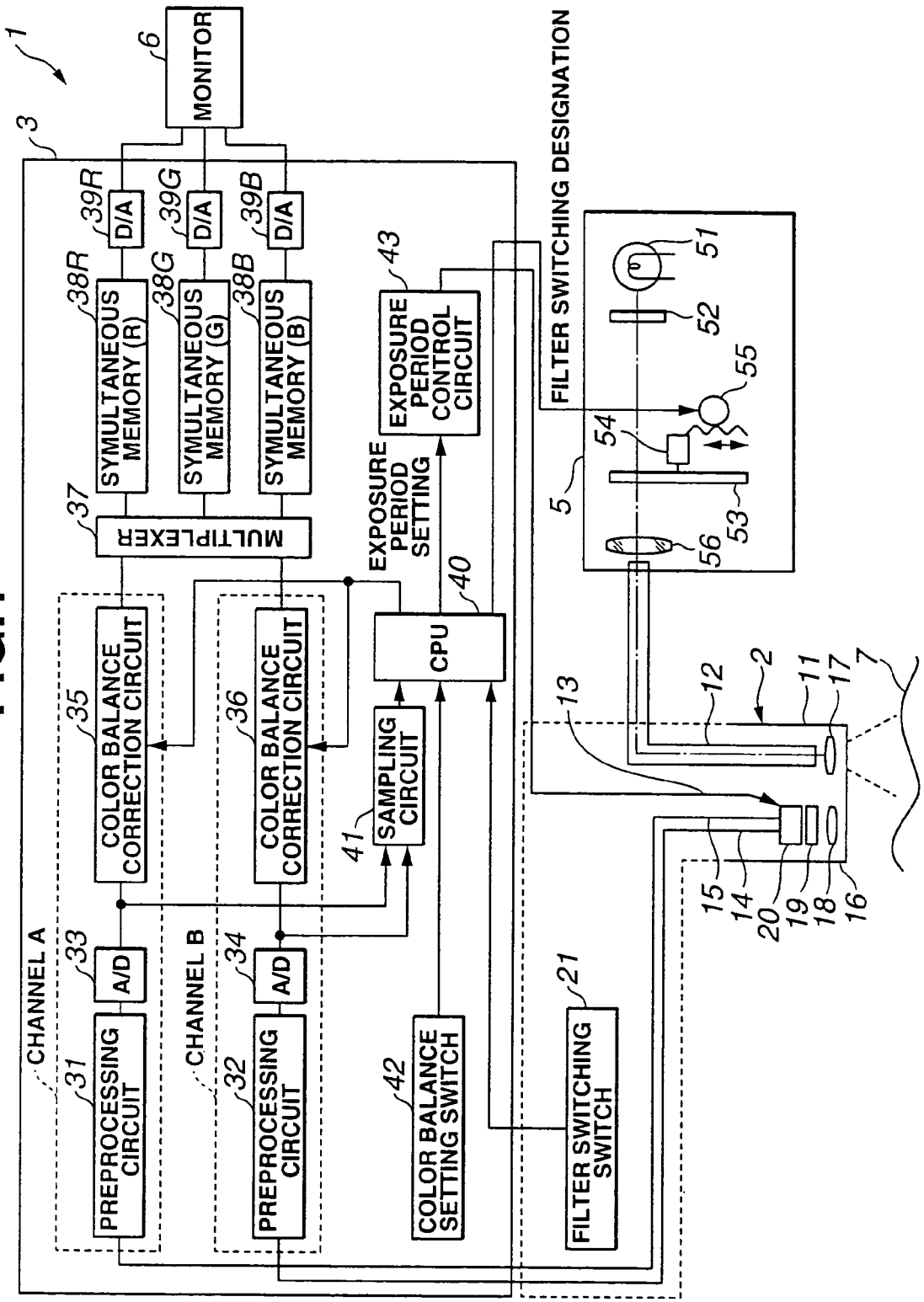
FIG. 1 is a block diagram illustrating the schematic configuration of the endoscope device of an embodiment of the present invention.
Figure 2:
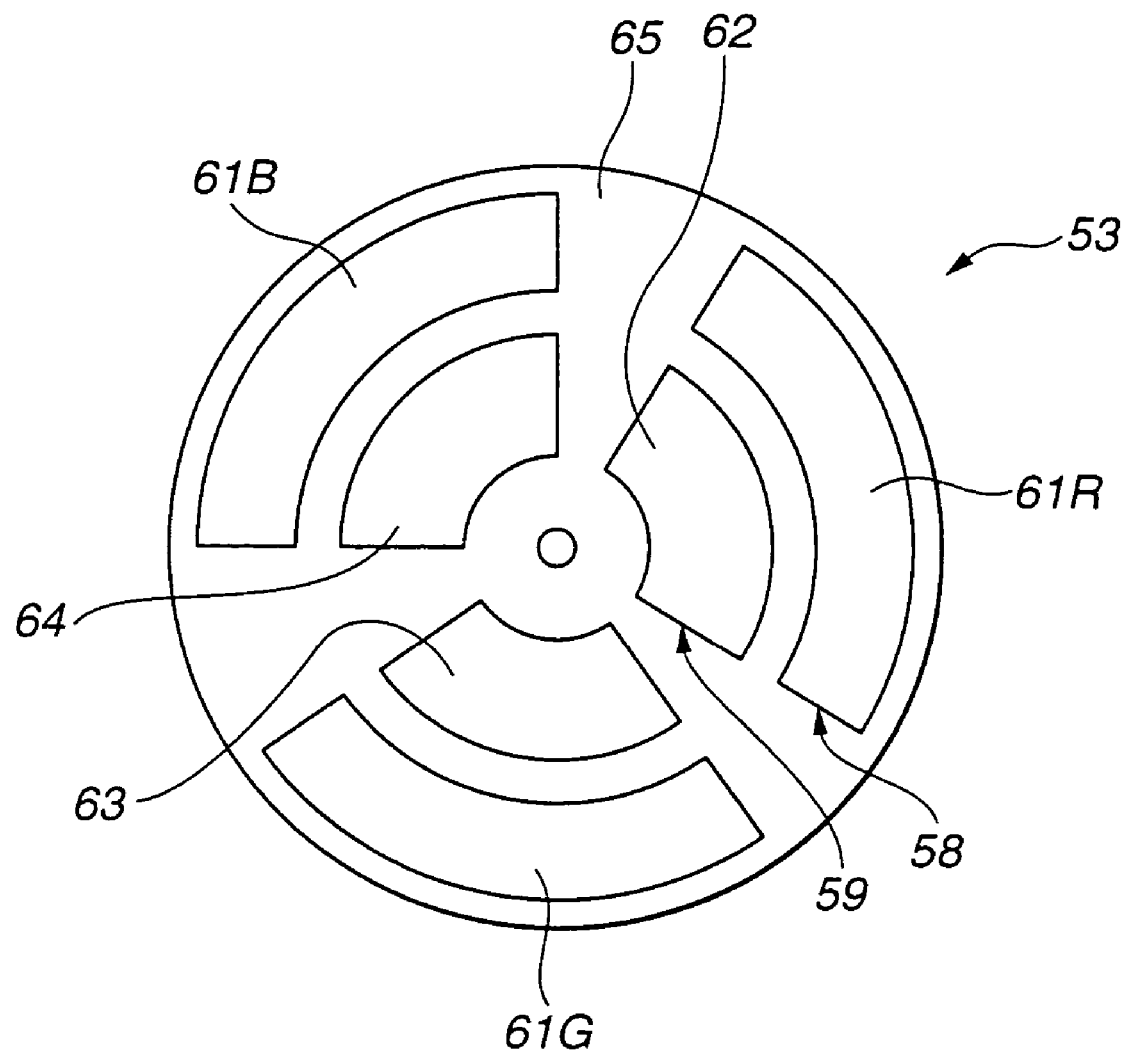
FIG. 2 is a plan view illustrating the configuration of a rotary filter plate in the embodiment.
Figure 3:
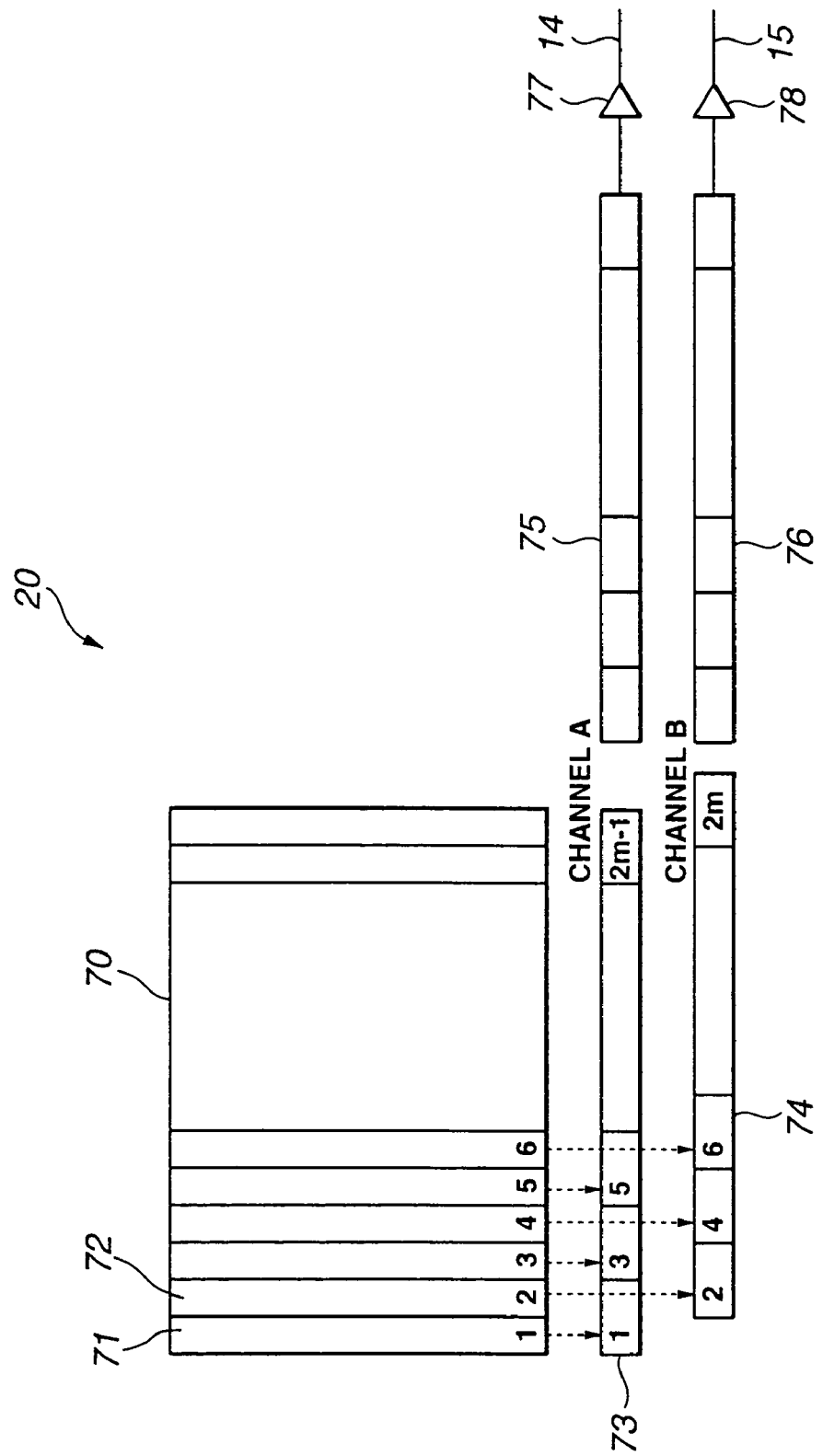
FIG. 3 is a block diagram of a CCD in the embodiment.
Figure 4:
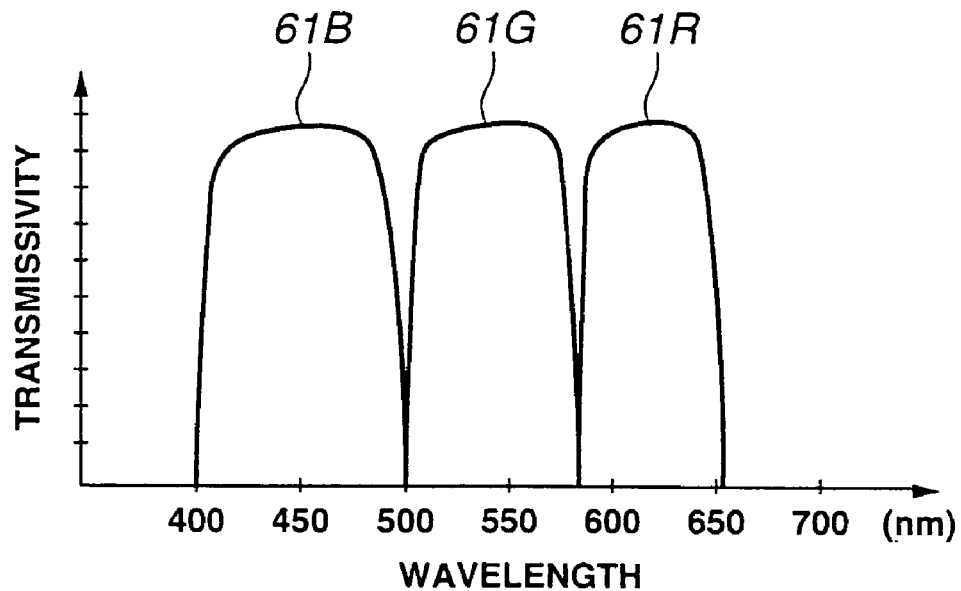
FIG. 4 is a graph illustrating the spectral characteristic of the outer circumferential filter in the embodiment.
Figure 5:
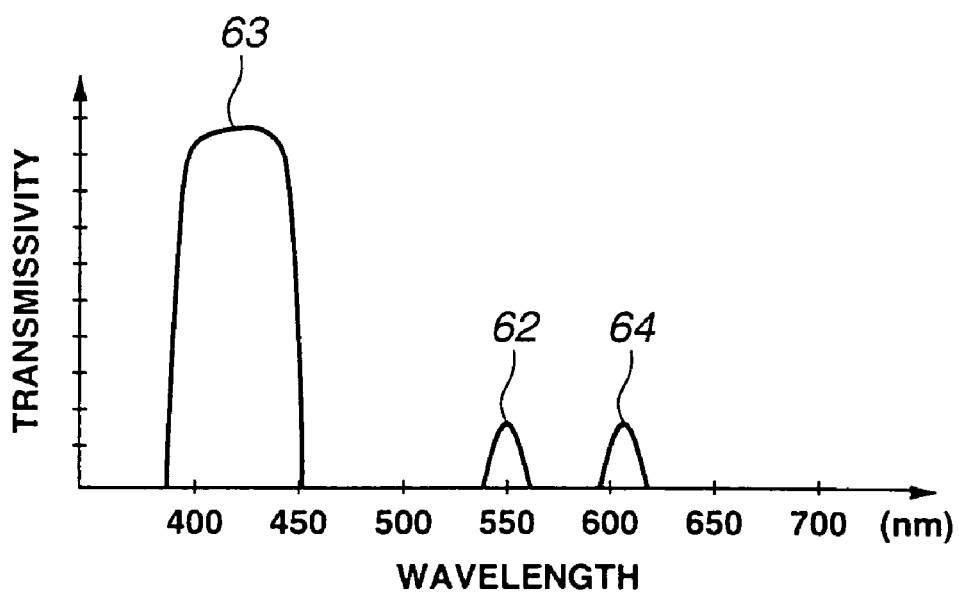
FIG. 5 is a graph illustrating the spectral characteristic of the inner circumferential filter in the embodiment.
Figure 6:
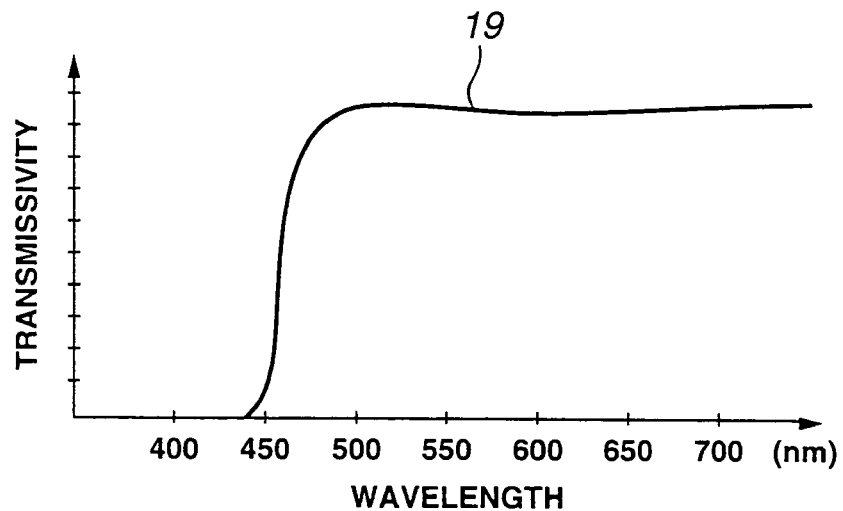
FIG. 6 is a graph illustrating the transmission characteristic of an excitation light cut-off filter in the embodiment.
Figure 7:
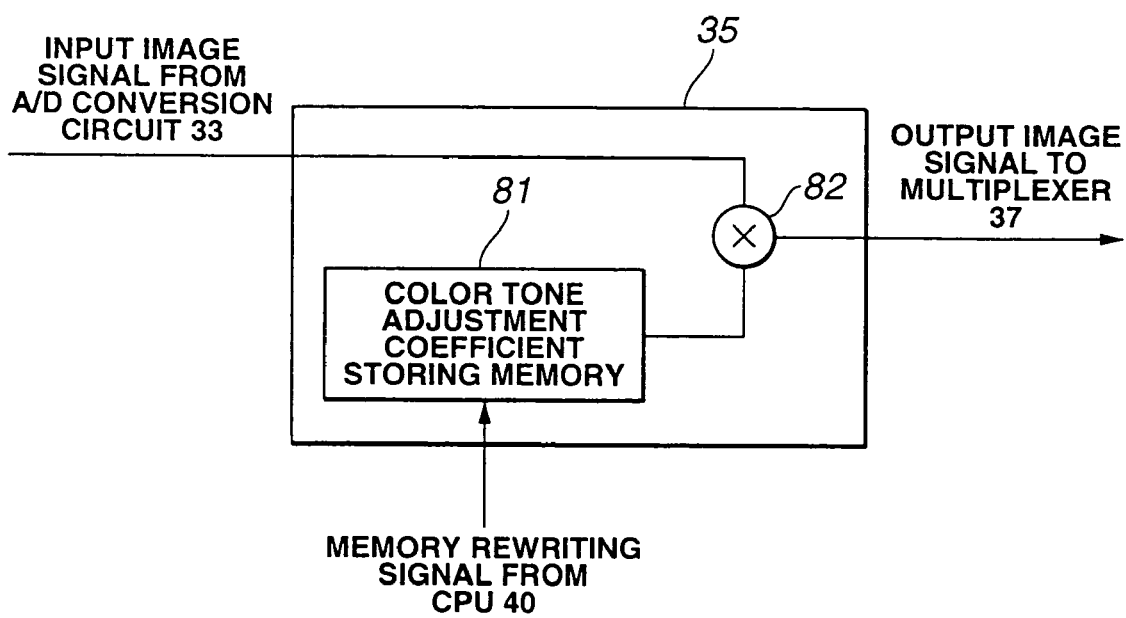
FIG. 7 is a block diagram illustrating a color balance correction circuit in the embodiment.
Figure 8:
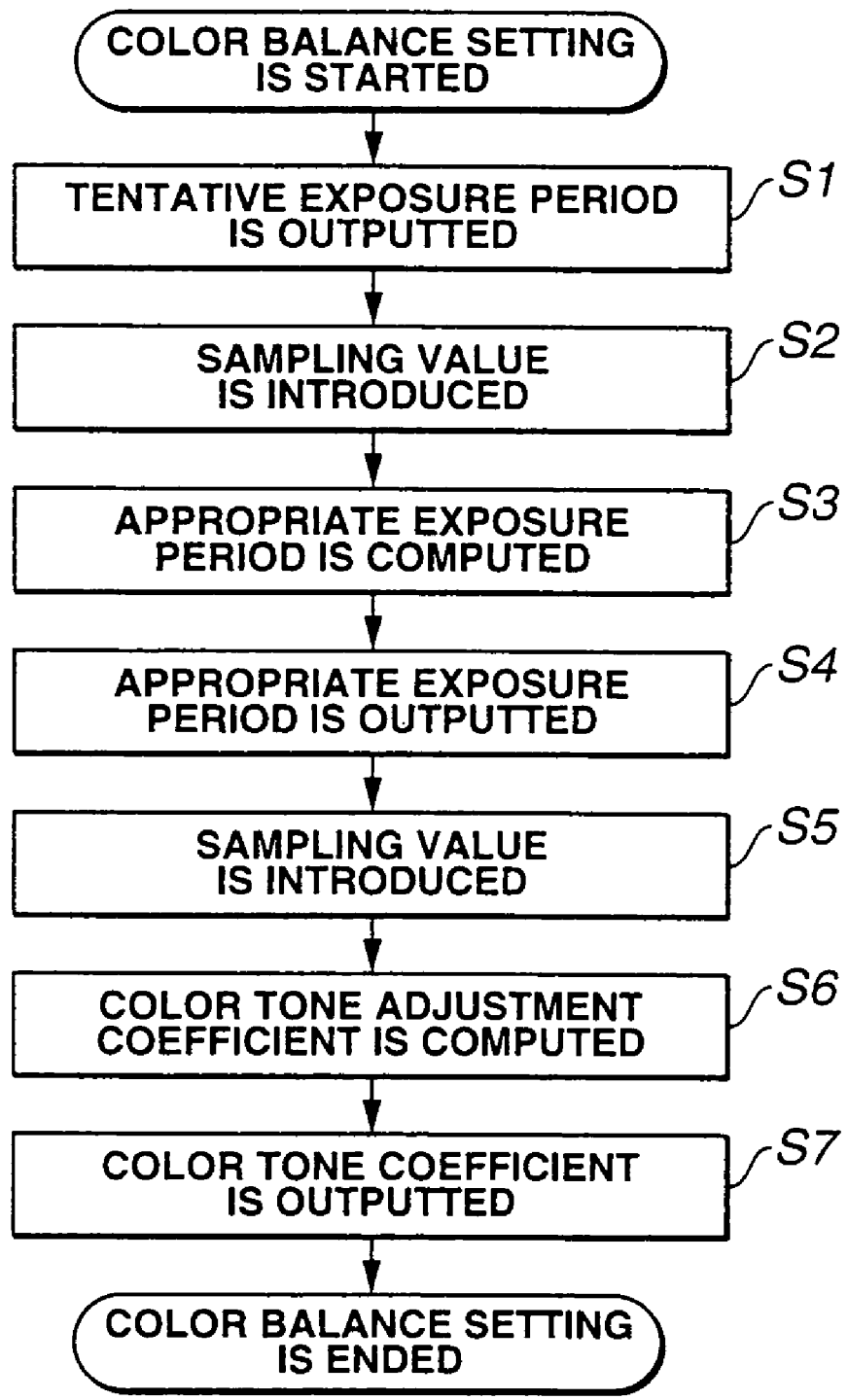
FIG. 8 is a flowchart illustrating the processing conducted when the color balance setting switch is pushed down in the embodiment.
Figure 9:
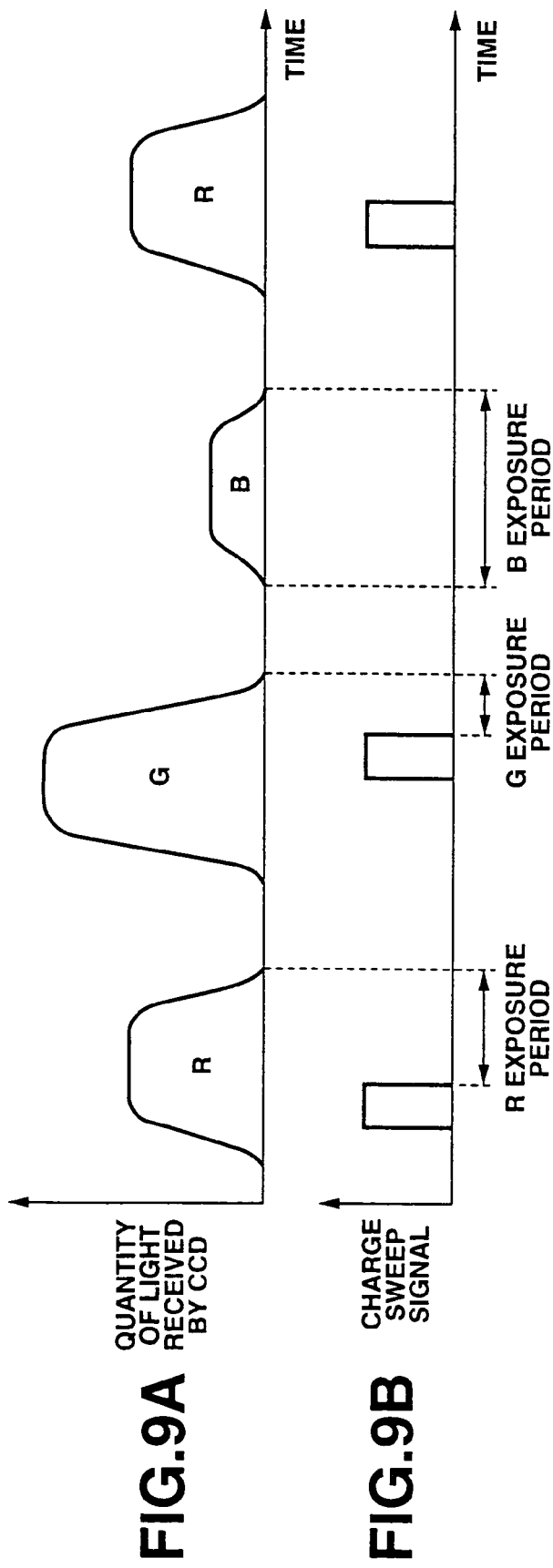
FIG. 9A is a timing chart illustrating the quantity of light received by the CCD and a charge sweep signal in the embodiment.
FIG. 9B is a timing chart illustrating the quantity of light received by the CCD and a charge sweep signal in the embodiment.
Figure 10:
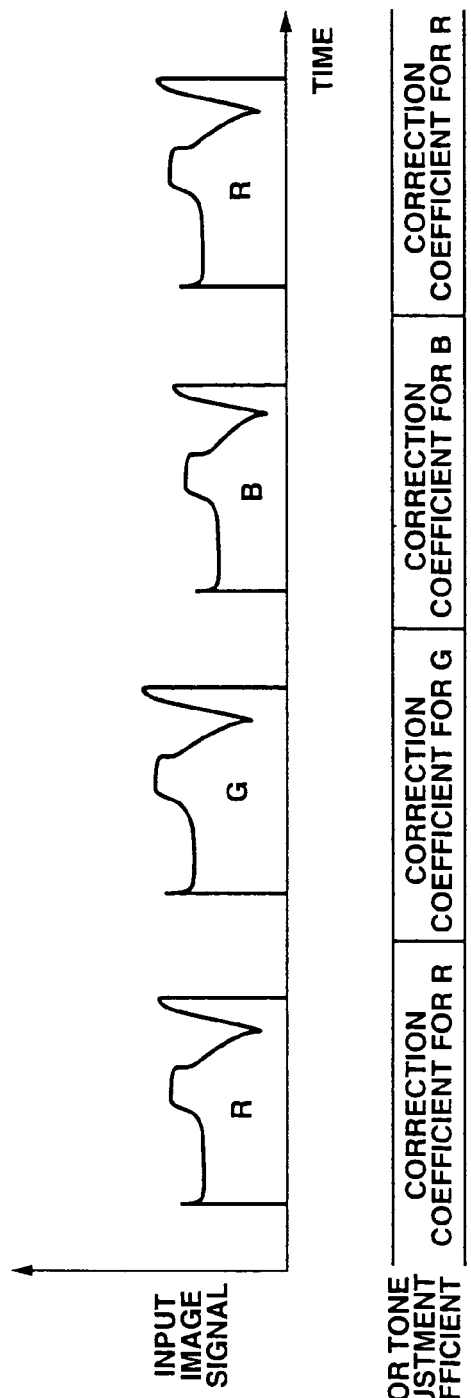
FIG. 10A is a timing chart illustrating an input image signal and a color tone adjustment coefficient in the embodiment.
FIG. 10B is a timing chart illustrating an input image signal and a color tone adjustment coefficient in the embodiment.

FIGS. 1 to 10B relate to an embodiment of the present invention. FIG. 1 is a block diagram illustrating schematically the configuration of the endoscope device. FIG. 2 is a plan view illustrating the configuration of a rotary filter plate. FIG. 3 is a block diagram of a solid state image pick-up element of a charge-coupled element type (referred to hereinbelow as CCD). FIG. 4 is a graph illustrating the spectral characteristic of the outer circumferential filter. FIG. 5 is a graph illustrating the spectral characteristic of the inner circumferential filter. FIG. 6 is a graph illustrating the transmission characteristic of an excitation light cut-off filter. FIG. 7 is a block diagram illustrating a color balance correction circuit. FIG. 8 is a flowchart illustrating processing conducted when the color balance setting switch is pushed down. FIG. 9A and FIG. 9B are timing charts illustrating the quantity of light received by the CCD and a charge sweep signal. FIG. 10A and FIG. 10B are timing charts illustrating an input image signal and a color tone adjustment coefficient.

As shown in FIG. 1, an electronic endoscope device 1 of the present embodiment comprises an electronic endoscope 2, a signal processing unit 3, a light source unit 5, and a monitor 6.

The electronic endoscope 2 comprises an elongated insertion portion 11 that can be inserted into a body cavity. A CCD 20 is contained in a distal end portion 16 of the insertion portion 11.

The electronic endoscope 2 is freely detachably connected to the signal processing unit 3. The signal processing unit 3 conducts signal processing of image signals obtained with the CCD 20.

The light source unit 5 serves to generate a light for observations. In the present embodiment, the light source unit 5 and signal processing unit 3 are provided as separate units. However, the light source unit 5 may be constructed so as to be incorporated in the signal processing unit 3.

The monitor 6 is connected to the signal processing unit 3 for displaying the image signals that are image processed in the signal processing unit 3.

The electronic endoscope 2 will be described hereinbelow in greater detail.

The electronic endoscope 2 comprises the elongated insertion portion 11 for insertion into a body cavity of a patient.

The insertion portion 11 is constituted of a soft portion when it is designed for conducting observations in a digestion tract, bronchial tube, head of neck (pharynx), bladder, or a rigid portion when it is used for abdominal cavity, thoracic cavity, or uterus.

A light guide 12, a charge sweep signal line 13, and CCD output signal lines 14, 15 are disposed inside the insertion portion 11.

The distal end side of the light guide 12, an illumination lens 17, an objective lens 18, an excitation light cut-off filter 19, and the CCD 20 are provided in a distal end portion 16 of the insertion portion 11.

The light guide fiber 12 transmits the illumination light from the light source unit 5 provided in the signal processing unit 3 and guides the light to the distal end portion 16 of the insertion portion 11.

The illumination lens 17 is provided in the distal end portion 16 of the insertion portion 11 and is disposed at the distal end surface side of the light guide fiber 12.

The illumination light that is guided by the light guide fiber 12 from the light source unit 5 illuminates an object 7 via the illumination lens 17.

The objective lens 18 serves for forming images by the light from the object 7.

The excitation light cut-off filter 19 is provided on the front surface of the CCD 20 and removes the excitation light by cutting off the light with a wavelength of 460 nm or less. That is, the excitation light cut-off filter 19 has a spectral characteristic such that it transmits auto-fluorescence generated by the living-body tissue (wavelength of about 500 nm or more) and does not transmit the excitation light.

The reflected light and auto-fluorescence from the object 7 form images on a light-receiving area 70 (see FIG. 3) of the CCD 20 via the objective lens 18 and excitation light cut-off filter 19.

The CCD 20 is an image sensor provided in the distal end portion 16 of the insertion portion 11 and disposed in the image-forming position of the objective lens 18.

In the present embodiment, the CCD 20 is disposed in a direct view configuration, but the CCD 20 can be also disposed in a slant view or side view configuration.

Furthermore, the CCD 20 is connected via the charge sweep signal line 13 to an exposure period control circuit 43 located inside the signal processing unit 3. The CCD 20 conducts electronic shutter control based on the charge sweep signal generated by the exposure period control circuit 43.

Furthermore, the CCD 20 also conducts signal charge accumulation, sensitivity control and reading in response to drive signals from a CCD drive circuit (not shown in the figure).

The object image formed on the light-receiving area 70 (see FIG. 3) of the CCD 20 by the objective lens 18 and excitation light cut-off filter 19 is photoelectrically converted by pixels of the CCD 20 and then transferred and outputted. The output signal from the CCD 20 is supplied via the CCD output signal lines 14, 15 to respective preprocessing circuits 31, 32 located inside the signal processing unit 3.

Further, in the electronic endoscope 2, a filter switch 21 is installed in the control unit at the proximal end side thereof. The filter switch 21 serves to designate switching of filters.

The operation signal of the filter switch 21 is supplied to a CPU 40 located in the signal processing unit 3.

The signal processing unit 3 comprises preprocessing circuits 31, 32, analog/digital conversion circuits (referred to hereinbelow as A/D conversion circuits) 33, 34, color balance correction circuits 35, 36, a multiplexer 37, simultaneous memories 38R, 38G, 38B, digital/analog conversion circuits (referred to hereinbelow as D/A conversion circuits) 39R, 39G, 39B, the CPU 40, a sampling circuit 41, a color balance setting switch 42, and the exposure period control circuit 43.

Here, the CCD output signal line 14, preprocessing circuit 31, A/D conversion circuit 33, and balance correction circuits 35 constitute a signal processing system of channel A for processing signals from odd-number lines 71 of the light-receiving area 70 shown in FIG. 3.

The CCD output signal line 15, preprocessing circuit 32, A/D conversion circuit 34, and balance correction circuits 36 shown in FIG. 1 constitute a signal processing system of channel B for processing signals from even-number lines 72 of the light-receiving area 70 shown in FIG. 3.

Further, as shown in FIG. 1, the signal processing unit 3 is configured such that image signals flow through in the order of the preprocessing circuits 31, 32, A/D conversion circuits 33, 34, color balance correction circuits 35, 36, multiplexer 37, simultaneous memories 38R, 38G, 38B, and D/A conversion circuits 39R, 39G, 39B.

Signals after A/D conversion conducted with the A/D conversion circuits 33, 34 are inputted in the sampling circuit 41.

The light source unit 5 comprises a xenon lamp (referred to hereinbelow as lamp) 51, an IR cut-off filter 52, a rotary filter plate 53, motors 54, 55, and a converging lens 56.

The lamp 51 emits the illumination light. The IR cut-off filter is provided on the illumination light path of the lamp 51 for restricting the transmission wavelength. The motor 54 rotates and drives the rotary filter plate 53. The motor 55 is employed for moving the rotary filter plate 53 in the direction perpendicular to the optical axis.

As shown in FIG. 2, the rotary filter plate 53 has a double structure in which filter sets 58, 59 are arranged in the outer circumferential portion and inner circumferential portion, respectively.

An R filter 61R, a G filter 61G, and a B filter 61B which transmit light of red (R), green (G), and blue (B) wavelength, respectively, are disposed on the outer circumference of the rotary filter plate 53.

Thus, the R filter 61R, G filter 61G, and B filter 61B constitute the outer circumferential filter set 58.

A G' filter 62 which transmits narrow-band light of 540-560 nm, an excitation filter 63 which transmits the excitation light of 390-450 nm, and an R' filter 64 which transmits a narrow band light of 600-620 nm are disposed on the inner circumference of the rotary filter plate 53.

That is, the G' filter 62, excitation filter 63, and R' filter 64 constitute an inner circumferential filter set 59.

Further, portions of the rotary filter plate 53 outside the zones where the filters are disposed are formed of members 65 that shield the light.

Spectral characteristics of the outer circumferential and inner circumferential filters of the rotary filter plate 53 will be described hereinbelow with reference to FIG. 4 and FIG. 5.

As shown in FIG. 4, the R filter 61R, G filter 61G, and B filter 61B located on the outer circumference have spectral distributions without gaps between respective transmission spectra.

As shown in FIG. 5, the G' filter 62, excitation filter 63, and R' filter 64 located on the inner circumference have discrete spectral distributions in which gaps are present.

As shown in FIG. 3, the CCD 20 comprises the light receiving area 70, horizontal transfer channels 73, 74, transfer channels 75, 76 equipped with a CMD (Charge Multiplying Device), and charge detection units 77, 78.

Furthermore, the transfer channels 75, 76 equipped with a CMD includes a plurality of cells, the number of those cells being almost equal to the number of cells of the horizontal transfer channels 73, 74.

A signal charge generated in each pixel of the light receiving area 70 is in a format that can be read separately in two channels A and B with the odd-number lines 71 and even-number lines 72 by means of vertical transfer pulses.

The signal charges that are read from the odd-number lines 71 and even-number lines 72 are transferred into horizontal transfer channels 73, 74 for respective horizontal lines and further transferred from the respective horizontal transfer channels 73, 74 into respective transfer channels 75, 76 equipped with a CMD by horizontal transfer pulses. Further, in the transfer channels 75, 76 equipped with a CMD, sensitivity control pulses are applied and signal amplification is carried out, while the signal charges are transferred through each cell by the horizontal transfer pulses. Therefore, each time the signal charges are transferred through the cell of the transfer channel equipped with a CMD, the amplification factor is increased in geometric series. The amplified signal charges are sequentially transferred into the charge detection units 77, 78. The charge detection units 77, 78 conduct charge-voltage conversion of charges from respective transfer channels 75, 76 equipped with a CMD into a voltage, and output the voltage into respective CCD output signal lines 14, 15.

With the above-described configuration, in the CCD 20, the CMD is disposed in a horizontal register and variable amplification can be conducted by sensitivity control pulses from the outside.

The excitation light cut-off filter 19 shown in FIG. 1 has a cut-off transmission characteristic which shields the light with a wavelength of 460 nm or less, as shown in FIG. 6.

The color balance correction circuit 35 shown in FIG. 1 has a color tone adjustment coefficient storing memory 81 and a digital multiplier 82, as shown in FIG. 7.

The color tone adjustment coefficient storing memory 81 conducts rewriting of the color tone adjustment coefficient based on the memory rewrite signals from the CPU 40 and supplies data on the color tone adjustment coefficients to one input terminal of a digital multiplier 82.

The input image signal from the A/D conversion circuit 33 is led to the other input terminal of the digital multiplier 82.

The digital multiplier 82 multiplies the input image signal from the A/D conversion circuit 33 by the color tone adjustment coefficient of the color tone adjustment coefficient storing memory 81 and outputs the product to one input terminal of the multiplexer 37.

Furthermore, the configuration of the color balance correction circuit 36 shown in FIG. 1 is identical to that of the color balance correction circuit 35 shown in FIG. 7, except that the input terminal 36 is connected to the A/D conversion circuit 34 and the output terminal is connected to the multiplexer 37.

The operation of the present embodiment will be described below.

Referring to FIG. 1, light for illuminating the object 7 is emitted from the lamp 51 of the light source unit 5. The light emitted from the lamp 51 passes through the IR cut-off filter 52, rotary filter plate 53, and converging lens 56 and is incident on the light guide fiber 12 of the electronic endoscope 2.

In this case, the IR cut-off filter 52 cuts off the IR rays, thereby preventing the filters on the rotary filter plate 53 from being illuminated by the unnecessary heat or light.

During normal light observations, the outer circumferential filter set 58 of the rotary filter plate 53 is disposed on the optical path and rotated at the prescribed rate by the motor 54.

As a result, the R filter 61R, G filter 61G, and B filter 61B are successively disposed on the optical path and transmit the red, green, and blue light, respectively. As a consequence, during normal light observations, the red, green, and blue light is successively emitted from the light source unit 5.

During fluorescent observations, the motor 55 moves the rotary filter plate 53 in the direction perpendicular to the optical axis in response to the signal from the filter position control circuit (not shown in the figure). As a result, the inner circumferential filter set 59 of the rotary filter plate 53 is inserted onto the optical path.

At the time of inserting the inner circumferential filter set 59, in a state in which the G' filter 62, excitation filter 63, and R' filter 64 are disposed on the optical path, the rotary filter plate 53 is rotated at the prescribed rate by the motor 54. As a result, the light source unit 5 successively emits light with a wavelength of 540-560 nm, 390-450 nm, and 600-620 nm.

Here, the light with a wavelength of 390-450 nm is excitation light for exciting the auto-fluorescence of the living-body tissue.

The light incident upon the light guide fiber 12 of the electronic endoscope illuminates the object 7, for example a digestive tract, via the illumination lens 17 of the distal end portion 16 of the insertion portion 11.

The light scattered, reflected, and emitted by the object 7 forms an image on the light receiving area 70 (see FIG. 3) of the CCD 20 via the objective lens 18 of the distal end portion 16 and picks up the image.

Here, the excitation light cut-off filter 19 shields the excitation light with a wavelength of 390-450 nm at the front surface of the CCD 20 and extracts the fluorescence.

The CCD 20 is driven by the CCD drive circuit (not shown in the figure) synchronously with the rotation of the rotary filter plate 53, and the image signals corresponding to the illumination light that has passed the respective filters of the rotary filter plate 53, such as the R filter 61R, G filter 61G, and B filter 61B, are outputted sequentially to the signal processing unit 3. The image signals that are outputted sequentially to the signal processing unit 3 serve as two systems of the A channel corresponding to odd-number lines 71 and the B channel corresponding to even-number lines 72.

Furthermore, if necessary, sensitivity control pulses from the sensitivity control pulse generation circuit (not shown in the figures) are inputted into the transfer channels 75, 76 equipped with a CMD in the CCD 20, to generate secondary electrons caused by impact ionization and amplify the signal charge. The amplification factor in this case is controlled by the amplitude of the sensitivity control pulses.

The image signals of the A channel and B channel inputted in the signal processing unit 3 are initially inputted in respective preprocessing circuits 31, 32. In the preprocessing circuits, 31, 32, the adequate image signals of the A channel and B channel are extracted by CDS (correlation double sampling) processing or the like.

The image signals of the A channel and B channel outputted from preprocessing circuits 31, 32 are converted from analog signals into digital signals with respective A/D conversion circuits 33, 34.

The digital signals of the images of the A channel and B channel that are outputted from the A/D conversion circuits 33, 34 are inputted in respective color balance compensation circuits 35, 36.

Color tone adjustment coefficients are written by the CPU 40 into the color tone correction coefficient storing memory 81 of the color balance correction circuits 35, 36, and the color balance correction circuits 35, 36 amplify the input signals at the prescribed amplification factor for each illumination wavelength based on color discrimination signals (not shown in the figure).

The multiplexer 37 combines the digital signals from the color balance correction circuits 35, 36 of images of the A channel and B channel into digital signals of the images of one system, separates the field sequential digital signals of the images into R (or narrow-band green reflected light), G (or fluorescence), and B (or narrow-band red reflected light) colors and outputs them to simultaneous memories 38R, 38G, and 38B, respectively.

In the simultaneous memories 38R, 38G, and 38B, simultaneity of field sequential digital signals is carried out by simultaneously reading the successively stored images. The simultaneous digital signals in respective R, G, B wavelength bands are subjected to conversion for correcting the gamma characteristic of the monitor in the gamma correction circuit (not shown in the figure), converted into analog signals by respective D/A conversion circuits 39R, 39G, and 39B, and displayed on the monitor 6.

During normal light observations, the red reflected light, green reflected light, and blue reflected light components are displayed on the respective RGB pixels of the monitor 6.

Furthermore, during fluorescent observations, the narrow-band green reflected light, fluorescence, and narrow-band red reflected light are displayed on the respective RGB pixels of the monitor 6.

On the other hand, in the exposure period control circuit 43, the exposure quantity in the CCD 20 is controlled by sending a charge sweep signal to the CCD 20. The charge sweep timing determined by the exposure period control circuit 43 is adjusted for each illumination wavelength of the illumination light.

Furthermore, if the filter switch 21 is pressed down by the operator, the pressing is recognized by the CPU 40, the motor 55 is driven by the CPU 40, the outer circumferential filter set 58 and inner circumferential filter set 59 of the rotary filter plate 53 are switched, and normal light observation and fluorescent observation are switched.

Simultaneously with this switching, the CPU 40 switches various settings in the signal processing unit 3 between those for normal light observations and those for fluorescent observations.

When the operator of the electronic endoscope device 1 adjusts the color balance during normal light observations, the operator initiates setting of color balance by pressing down the color balance setting switch 42 in a state in which the image of the white reference body is picked up.

The processing conducted when the color balance setting switch 42 is pressed down will be described below with reference to FIG. 8.

As shown in FIG. 8, if the color balance setting switch is pressed down in a normal light observation mode, first, in step S1, the CPU 40 provides a maximum exposure period as a tentative exposure period to the exposure period control circuit 43 for image signals of all the RGB wavelength bands. That is, the exposure period control circuit 43 terminates the electronic shutter function of the CCD 20. As a result, the quantity of each of RGB colors received by the CCD 20 is as shown in FIG. 9A.

Then, in step S2, the CPU 40 acquires the brightness of the image sampled with the sampling circuit 41 for each RGB.

Then, in step S3, the CPU 40 computes the appropriate exposure period based on the sampling data of channel A. Here, the object is to set a rough color balance. Therefore, the RGB exposure period is computed such that the RGB amplification factor ratio becomes 1/Vr:1/Vg:1/Vb, where Vr, Vg, and Vb stand for sampling values of respective RGB images. At this time, it is preferred that the electronic shutter of the CCD 20 be not used when the exposure period in RGB is maximum to ensure a high brightness.

Figure 11:
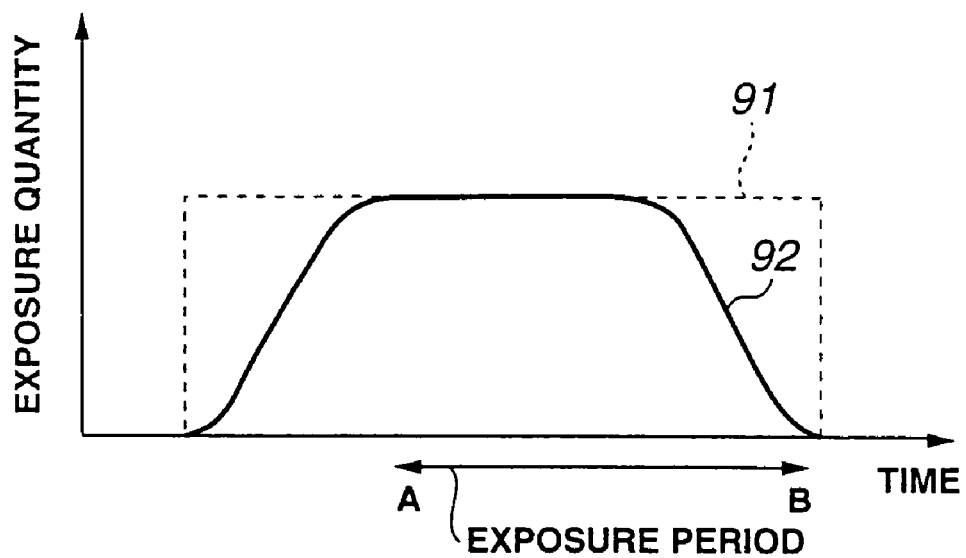
FIG. 11 is a graph illustrating the relationship between the exposure quantity and exposure period with respect to the conventional rotary filter.
Figure 12:
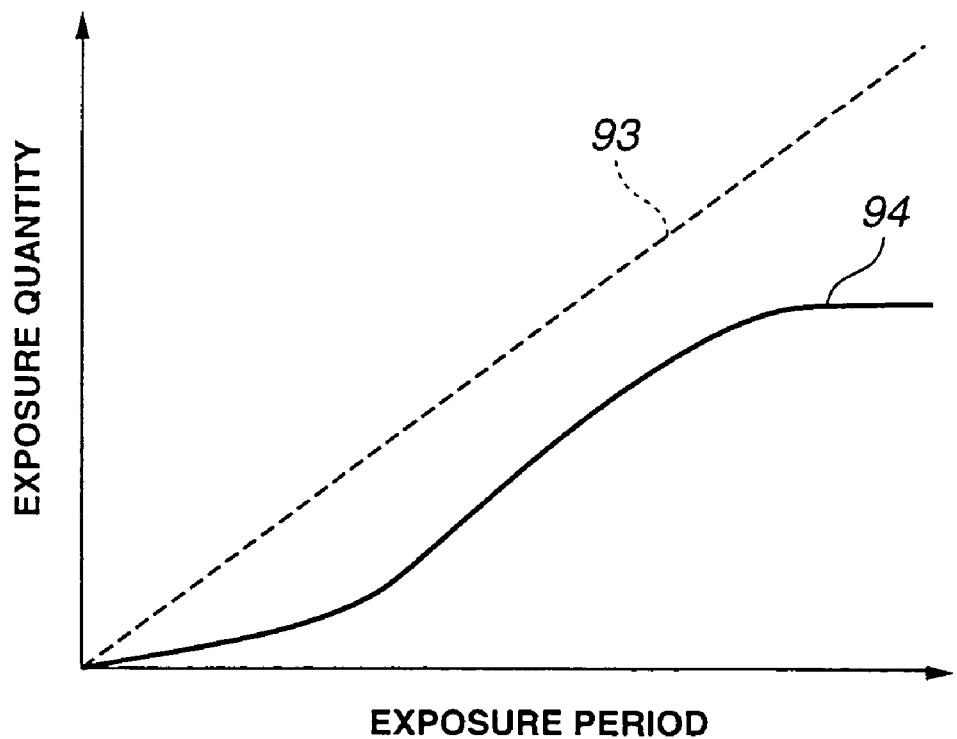
FIG. 12 is a graph illustrating the relationship between the exposure quantity and exposure period with respect to the conventional rotary filter.

Then, in step S4, the CPU 40 outputs the exposure period computed in step S3 to the exposure period control circuit 43. As a result, the exposure period control circuit 43 sends the charge sweep signal shown in FIG. 9B to the CCD 20 so as to obtain the aforementioned computed exposure period. Even if the exposure period is thus set, the probability of the color balance taking an exactly desirable ratio is low, due to the reasons explained with reference to FIG. 11 and FIG. 12.

Then, in step S5, the CPU 40 again acquires the RGB values sampled with the sampling circuit 41 in order to conduct accurate color balance adjustment and adjustment between channels A and B.

Then, in step S6, the CPU 40 computes the color tone adjustment coefficients that will be set in the color balance correction circuits 35, 36. Here, the color tone adjustment coefficients are calculated such that the RGB amplification factor ratio becomes 1/Vr':1/Vg':1/Vb', where Vr', Vg', and Vb' stand for sampling values of respective RGB images.

Then, in step S7, the CPU 40 stores the color tone adjustment coefficients computed in step S6 in separate areas of the color tone adjustment coefficient storing memory 81 for each observation mode and each RGB shown in FIG. 7. In this way, the color balance setting is completed.

With such a processing, the color balance correction circuit 35 carries out even more strict correction of color balance that is in general corrected by the exposure period control.

When image-picking-up by the normal light is thereafter carried out with the electronic endoscope device 1, the color balance correction circuit 35 multiplies with the digital multiplier 82 the color tone adjustment coefficients shown in FIG. 10B that are stored in separate areas of the color tone adjustment coefficient storing memory 81 for each observation mode and each RGB and the image signals, shown in FIG. 10A, that are picked up according to the observation mode and rotation of the rotary filter 53 and input from the A/D conversion circuit 33. As a result, the respective RGB image signals that are subjected to strict color balance correction are amplified at the above-described amplification factor ratio and outputted from the color balance correction circuit 35.

Further, as for the color balance correction circuit 36 of the B channel, in addition to color balance adjustment, the color tone correction coefficients are calculated so as to cancel the interchannel variance to the A channel. In other aspects, the operation of the color balance correction circuit 36 of the B channel is identical with the operation of the color balance correction circuit 35 of the A channel.

When the operator of the electronic endoscope device 1 adjusts color balance during fluorescent observations, the color balance setting is initiated by pressing down the color balance switch 22 in a state in which the insertion portion 11 is inserted into a body cavity and a normal mucous membrane of the patient is picked up in a fluorescent observation mode. Subsequent operations are identical to those conducted during normal observations.

The electronic endoscope 2 comprises an image pick-up unit (CCD 20) for picking up the image of the object 7 for each wavelength band of the illumination light that illuminates the object.

The color balance correction circuits 35, 36 serve as amplification means for amplifying the signals relating to the object 7 that are output from the CCD 20, for the each wavelength band.

The exposure period control circuit 43 serves as exposure period setting means for setting the exposure period of the CCD 20 for the each wavelength band.

Furthermore, the CPU 40 serves as amplification factor setting means for setting the amplification factors of the color balance correction circuits 35, 36 for the each wavelength band based on the signals corresponding to the object 7 that are picked up by the CCD 20 according to the exposure period that is set by the exposure period setting means.

The monitor 6 serves as a display unit for color displaying the video images corresponding to the signals that are amplified by the color balance correction circuits 35, 36.

The color balance setting switch 42 serves as color balance setting designation means for designating the color balance adjustment of the video images that will be displayed by the monitor 6.

The aforementioned exposure period setting means sets the exposure period for the each wavelength band based on the video signal that is outputted by the CCD 20 based on the designation of the color balance setting switch 42.

With the afore-described embodiment, the correction of color balance is conducted by the exposure period control. Therefore, it becomes unnecessary to conduct amplification at a high amplification factor for a specific color, and noise influence can be reduced for all the color components. Furthermore, because the amplification factor control is also used for correcting the color balance, slight color balance errors following the exposure period control can be also corrected and setting of color balance can be conducted with even better accuracy. Therefore a better image with a low noise can be obtained under an accurately set color balance.

Furthermore, in the present embodiment, the exposure period is set based on the designation of the color balance setting switch 42 serving as color balance setting designation means. Therefore, the amplification factors for all the colors become almost equal and the noise influence can be greatly reduced for all the color components, regardless of the spread during the production of optical filters.

Moreover, with the present embodiment, an especially significant effect in terms of suppressing the noise influence is attained due to application to the electronic endoscope device 1 for fluorescence which is easily affected by the noise induced by the variety of optical filters.

Further, in the present embodiment, an especially significant effect in terms of suppressing the noise influence is attained because of the application to the electronic endoscope device 1 for illumination of the illumination light having a discrete spectral distribution shown in FIG. 5, which is easily affected by the noise induced by the variety of optical filters.

Moreover, in the present embodiment, the application to the electronic endoscope device 1 that allows the observation of fluorescence in a visual range is considered, but applications to reflected light observations, IR ray observations, and fluorescence observations in an IR range that used three discrete narrow-band wavelengths, as disclosed in Japanese Patent Application Laid-open No. 2002-95635, are also possible.

Further, in the present embodiment, the amplification for color balance adjustment is conducted inside the signal processing unit 3, but the amplification may be also carried out in the transfer channels 75, 76 equipped with a CMD which are located inside the CCD 20.

The ratio of colors which are adjusted is not limited to 1:1:1 and a lesion portion can be also effectively recognized, for example, by displaying the normal mucous membrane of the patient as slightly greenish during fluorescent observations.

Computation of the exposure period is not limited to a computation method assuming a simple linearity of the exposure period and quantity of exposure, and noise can be effectively suppressed by conducting approximation to other functions to increase accuracy.

Further, the color balance setting switch is not limited to that located in the signal processing unit main body, it may be provided in the operation unit of the electronic endoscope 2 and also may be in the form of a foot switch which is operated by foot.

Embodiments constituted by partially combining the above-described embodiments are also within the scope of the present invention.

In this invention, it is apparent that working modes different in a wide range can be formed on the basis of this invention without departing from the spirit and scope of the invention. This invention is not restricted by any specific embodiment except being limited by the appended claims.

What is claimed is:

1. An electronic endoscope device comprising:
   an image pick-up unit capable of acquiring an object image with respect to illumination light employed for illuminating the object for each prescribed wavelength band, the object image being divided between at least a first channel and a second channel, each channel having a preprocessing circuit and a color balance correction circuit;
   a light supply unit having a rotary optical filter for successively supplying illumination light of different wavelength bands, the rotary optical filter being segmented into a plurality of individual wavelength filters defining a wavelength illumination period for each of the different wavelength bands;
   an exposure period setting circuit for individually setting the exposure period of the image pick-up unit corresponding to the each wavelength band in response to adjustment coefficients generated by the color balance correction circuit and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up image signals from the image pick-up unit;
   an amplifier for amplifying the picked-up image signals of the object image obtained with the image pick-up unit corresponding to the each wavelength band; and
   a control circuit for controllably amplifying the picked-up image signals acquired at the exposure period corresponding to the each wavelength band at computed amplification factors corresponding to the individual exposure period set for the each wavelength band.

2. The electronic endoscope device according to claim 1, further comprising:
   a display unit for color displaying the images corresponding to the signals amplified by the amplifier; and
   a color balance setting designation unit for designating balance adjustment of the colors of the images displayed by the display unit, wherein
   the exposure period setting circuit sets the exposure period corresponding to the each wavelength band according to image signals outputted by at least the preprocessing circuit of the first channel and the preprocessing circuit of the second channel based on the designation of the color balance setting designation unit.

3. The electronic endoscope device according to claim 2, wherein the image pick-up unit illuminates the object with excitation light and picks up an image of the object by fluorescent light from the object.

4. The electronic endoscope device according to claim 2, comprising:
the image pick-up unit illuminates the object with illumination light of a wavelength band having a discrete spectral distribution and picks up an image of the object by the light reflected from the object.

5. The electronic endoscope device according to claim 1, wherein the image pick-up unit illuminates the object with excitation light and picks up an image of the object by fluorescent light from the object.

6. The electronic endoscope device according to claim 1, wherein the image pick-up unit illuminates the object with illumination light of a wavelength band having a discrete spectral distribution and picks up an image of the object by the light reflected from the object.

7. The electronic endoscope device according to claim 1, wherein the exposure period setting circuit sets the exposure period with the electronic shutter for restricting an exposure period set by the rotary optical filter.

8. An electronic endoscope device comprising:
an image pick-up means capable of acquiring an object image with respect to illumination light employed for illuminating the object for each prescribed wavelength band, the object image being divided between at least a first channel and a second channel, each channel having a preprocessing means and a color balance correction means;
a light supply means having a rotary optical filter for successively supplying illumination light of different wavelength bands, the rotary optical filter being segmented into a plurality of individual wavelength filters defining a wavelength illumination period for each of the different wavelength bands;
an exposure period setting means for individually setting the exposure period of the image pick-up means corresponding to the each wavelength band in response to adjustment coefficients generated by the color balance correction means and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up image signals from the image pick-up means;
amplification means for amplifying picked-up image signals of the object image obtained with the image pick-up means corresponding to the each wavelength band; and
control means for controllably amplifying the picked-up image signals acquired at the exposure period corresponding to the each wavelength band at computed amplification factors corresponding to the individual exposure period for the each wavelength band.

9. The electronic endoscope device according to claim 8, further comprising:
display means for color displaying the images corresponding to the signals amplified by the amplification means; and
color balance setting designation means for designating balance adjustment of the colors of the images displayed by the display means, wherein
the exposure period setting means sets the exposure period corresponding to the each wavelength band according to image signals outputted by at least the preprocessing means of the first channel and the preprocessing means of the second channel based on the designation of the color balance setting designation means.

10. The electronic endoscope device according to claim 9, wherein the image pick-up means illuminates the object with excitation light and picks up an image of the object by fluorescent light from the object.

11. The electronic endoscope device according to claim 9, wherein: the image pick-up means illuminates the object with illumination light of a wavelength band having a discrete spectral distribution and picks up an image of the object by the light reflected from the object.

12. The electronic endoscope device according to claim 8, wherein the image pick-up means illuminates the object with excitation light and picks up an image of the object by fluorescent light from the object.

13. The electronic endoscope device according to claim 8, wherein the image pick-up means illuminates the object with illumination light of a wavelength band having a discrete spectral distribution and picks up an image of the object by the light reflected from the object.

14. The electronic endoscope device according to claim 8, wherein the exposure period setting means sets the exposure period with the electronic shutter for restricting an exposure period set by the rotary optical filter.

15. A signal processing device for processing signals corresponding to an object which are outputted by an endoscope comprising an image pick-up unit, the signal processing device comprising:
at least a first channel and a second channel, each channel having a preprocessing circuit and a color balance correction circuit, the signals corresponding to the object being divided between at least the first channel and the second channel;
a light supply unit having a rotary optical filter for successively supplying illumination light of different wavelength bands, the rotary optical filter being segmented into a plurality of individual wavelength filters defining a wavelength illumination period for each of the different wavelength bands;
an exposure period setting circuit for individually setting the exposure period of the image pick-up unit corresponding to the each wavelength band in response to adjustment coefficients generated by the color balance correction circuit and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up image signals from the image pick-up unit;
an amplifier for amplifying the picked-up image signals of the object image obtained with the image pick-up unit corresponding to the each wavelength band, the amplifier being a component of the color balance correction circuit of each channel; and
a control circuit for controllably amplifying the picked-up image signals acquired at the exposure period corresponding to the each wavelength band at computed amplification factors corresponding to the individual exposure period for the each wavelength band.

16. The signal processing device according to claim 15, wherein the exposure period setting circuit sets the exposure period corresponding to the each wavelength band according to image signals outputted by at least the preprocessing circuit of the first channel and the preprocessing circuit of the second channel based on a color balance setting designation which designates balance of the colors of the images displayed by a display unit.

17. The signal processing device according to claim 15, wherein the exposure period setting circuit sets the exposure period with the electronic shutter for restricting an exposure period set by the rotary optical filter.

18. An electronic endoscope device comprising:
illumination light supply means having a rotary optical filter for successively supplying light of different wavelength bands for illuminating an object, the rotary optical filter being segmented into a plurality of individual wavelength filters defining a wavelength illumination period for each of the different wavelength bands;
image pick-up means for successively picking up the images of the object for the each wavelength band, the images being divided between at least a first channel and a second channel, each channel having a preprocessing means and a color balance correction means;
amplification means for amplifying signals that are picked up by the image pick-up means, the amplification means being a component of the color balance correction means of each channel;
a display unit for color displaying the signals amplified by the amplification means;
exposure period setting means for individually setting the exposure period of the image pick-up means for the each wavelength band in response to adjustment coefficients generated by the color balance correction means and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up signals from the image pick-up means; and
amplification factor setting means for setting amplification factors in the each wavelength band in the amplification means based on the signals outputted from the image pick-up means after setting the exposure period.

19. The electronic endoscope device according to claim 18 further comprising:
color balance setting designation means for designating balance setting of the colors displayed by the display device, wherein
the exposure period setting means sets the exposure period for the each wavelength band based on the signals outputted by at least the preprocessing means of the first channel and the preprocessing means of the second channel corresponding to the designation of the color balance setting designation means.

20. The electronic endoscope device according to claim 19, wherein the light source means emits light of a wavelength exciting the object, and the image pick-up means picks up an image of the object by fluorescent light from the object.

21. The electronic endoscope device according to claim 19, wherein the different wavelength bands have a discrete spectral distribution.

22. The electronic endoscope device according to claim 19, wherein at least one exposure period which is set for the each wavelength band is an exposure period obtained by stopping the electronic shutter.

23. The electronic endoscope device according to claim 18, wherein the light source means emits light of a wavelength exciting the object, and the image pick-up means picks up an image of the object by fluorescent light from the object.

24. The electronic endoscope device according to claim 18, wherein the different wavelength bands have a discrete spectral distribution.

25. The electronic endoscope device according to claim 18, wherein at least one exposure period which is set for the each wavelength band is an exposure period obtained by stopping the electronic shutter.

26. The electronic endoscope device according to claim 18, wherein the exposure period setting means sets the exposure period with the electronic shutter for restricting an exposure period set by the rotary optical filter.

27. A color balance adjustment method in an electronic endoscope device for successively illuminating an object with illumination light having different wavelength bands and picking up the images of the object for each wavelength band of this illumination light employed for illumination, comprising the steps of:
picking up the images of the object for each wavelength band based on a prescribed exposure period;
successively supplying illumination light of different wavelength bands using a rotary optical filter, the rotary optical filter being segmented into a plurality of individual wavelength filters defining a wavelength illumination period for each of the different wavelength bands;
setting the exposure period individually for each wavelength band based on a brightness of image signals that correspond to the object image in each wavelength bandy and variably adjusting a generation time of an initial charge sweep signal during each wavelength illumination period for adjusting a staffing point of the exposure period within each wavelength illumination period, the exposure period of the each wavelength band terminating with a second charge sweep signal coinciding with termination of the wavelength illumination period, the second charge sweep signal transferring picked-up image signals;
picking up the images of the object based on the exposure period for each wavelength band that is set;
dividing each picked up image between at least a first channel and a second channel, each channel separately preprocessing and color balance correcting the divided picked up images;
computing the amplification factor of the image signals for each wavelength band based on the brightness of the image signal corresponded to the object that is picked up using the set exposure period; and
amplifying the image signals for the each wavelength band based on the computed amplification factor, said amplifying providing the color balance correction.

28. The color balance adjustment method according to claim 27, wherein the exposure period is set with the electronic shutter for restricting an exposure period set by the rotary optical filter.

29. An electronic endoscope device comprising:
   an image pick-up unit capable of acquiring an object image with respect to illumination light employed for illuminating the object for each prescribed wavelength band;
   a light supply unit having a rotary optical filter for successively supplying illumination light of different wavelength bands, the rotary optical filter being segmented into a plurality of individual wavelength filters defining a wavelength illumination period for each of the different wavelength bands;
   an exposure period setting circuit for individually setting the exposure period of the image pick-up unit corresponding to the each wavelength band in response to adjustment coefficients and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up image signals from the image pick-up unit;
   a color balance correction circuit having an amplifier for adjusting color balance of the object image and amplifying the picked-up image signals of the object image obtained with the image pick-up unit corresponding to the each wavelength band; and
   a control circuit for controllably amplifying the picked-up image signals acquired at the exposure period corresponding to the each wavelength band at computed amplification factors corresponding to the individual exposure period for the each wavelength band.

30. The electronic endoscope device according to claim 29, further comprising:
   a display unit for color displaying the images corresponding to the signals amplified by the amplifier; and
   a color balance setting designation unit for designating balance adjustment of the colors of the images displayed by the display unit, wherein the exposure period setting circuit sets the exposure period corresponding to the each wavelength band according to image signals outputted by the image pick-up unit based on the designation of the color balance setting designation unit.

31. The electronic endoscope device according to claim 30, wherein the image pick-up unit illuminates the object with excitation light and picks up an image of the object by fluorescent light from the object.

32. The electronic endoscope device according to claim 30, comprising:
   the image pick-up unit illuminates the object with illumination light of a wavelength band having a discrete spectral distribution and picks up an image of the object by the light reflected from the object.

33. The electronic endoscope device according to claim 29, wherein the image pick-up unit illuminates the object with excitation light and picks up an image of the object by fluorescent light from the object.

34. The electronic endoscope device according to claim 29, wherein the image pick-up unit illuminates the object with illumination light of a wavelength band having a discrete spectral distribution and picks up an image of the object by the light reflected from the object.

35. The electronic endoscope device according to claim 29, wherein the exposure period setting circuit sets the exposure period with the electronic shutter for restricting an exposure period set by the rotary optical filter.

36. An electronic endoscope device comprising:
   an image pick-up means capable of acquiring an object image with respect to illumination light employed for illuminating the object for each prescribed wavelength band;
   a light supply means having a rotary optical filter for successively supplying illumination light of different wavelength bands, the rotary optical filter being segmented into a plurality of individual wavelength filters defining a wavelength illumination period for each of the different wavelength bands;
   an exposure period setting means for individually setting the exposure period of the image pick-up means corresponding to the each wavelength band in response to adjustment coefficients and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up image signals from the image pick-up means;
   a color balance correction means having an amplification means for adjusting color balance of the object image and amplifying the picked-up image signals of the object image obtained with the image pick-up means corresponding to the each wavelength band; and
   control means for controllably amplifying the picked-up image signals acquired at the exposure period corresponding to the each wavelength band at computed amplification factors corresponding to the individual exposure period for the each wavelength band.

37. The electronic endoscope device according to claim 36, further comprising:
   display means for color displaying the images corresponding to the signals amplified by the amplification means; and
   color balance setting designation means for designating balance adjustment of the colors of the images displayed by the display means, wherein
   the exposure period setting means sets the exposure period corresponding to the each wavelength band according to image signals outputted by the image pick-up means based on the designation of the color balance setting designation means.

38. The electronic endoscope device according to claim 37, wherein the image pick-up means illuminates the object with excitation light and picks up an image of the object by fluorescent light from the object.

39. The electronic endoscope device according to claim 37, wherein: the image pick-up means illuminates the object with illumination light of a wavelength band having a discrete spectral distribution and picks up an image of the object by the light reflected from the object.

40. The electronic endoscope device according to claim 36, wherein the image pick-up means illuminates the object with excitation light and picks up an image of the object by fluorescent light from the object.

41. The electronic endoscope device according to claim 36, wherein the image pick-up means illuminates the object with illumination light of a wavelength band having a discrete spectral distribution and picks up an image of the object by the light reflected from the object.

42. The electronic endoscope device according to claim 36, wherein the exposure period setting means sets the exposure period with the electronic shutter for restricting an exposure period set by the rotary optical filter.

43. A signal processing device for processing signals corresponding to an object which are outputted by an endoscope comprising an image pick-up unit, the signal processing device comprising:
a light supply unit having a rotary optical filter for successively supplying illumination light of different wavelength bands, the rotary optical filter being segmented into a plurality of individual wavelength filters defining a wavelength illumination period for each of the different wavelength bands;
an exposure period setting circuit for individually setting the exposure period of the image pick-up unit capable of acquiring an object image with respect to illumination light employed for illuminating the object for each prescribed wavelength band, corresponding to the each wavelength band in response to adjustment coefficients and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up image signals from the image pick-up unit;
a color balance correction means having an amplifier for adjusting color balance of the object image and for amplifying the picked-up image signals of the object image obtained with the image pick-up unit corresponding to the each wavelength band; and
a control circuit for controllably amplifying the picked-up image signals acquired at the exposure period corresponding to the each wavelength band at computed amplification factors corresponding to the individual exposure period for the each wavelength band.

44. The signal processing device according to claim 43, wherein the exposure period setting circuit sets the exposure period corresponding to the each wavelength band according to image signals outputted by the image pick-up unit based on a color balance setting designation which designates balance of the colors of the images displayed by a display unit.

45. The signal processing device according to claim 43, wherein the exposure period setting circuit sets the exposure period with the electronic shutter for restricting an exposure period set by the rotary optical filter.

46. An electronic endoscope device comprising:
illumination light supply means having a rotary optical filter for successively supplying light of different wavelength bands for illuminating an object, the rotary optical filter being segmented into a plurality of individual wavelength filters defining a wavelength illumination period for each of the different wavelength bands;
image pick-up means for successively picking up the images of the object for the each wavelength band;
a color balance correction means having an amplification means for adjusting color balance of the object image and for amplifying signals that are picked up by the image pick-up means;
a display unit for color displaying the signals amplified by the amplification means;
exposure period setting means for individually setting the exposure period of the image pick-up means for the each wavelength band in response to adjustment coefficients generated by the color balance correction means and variably adjusting a generation time of an initial charge sweep signal during each wavelength illumination period for adjusting a starting point of the exposure period within each wavelength illumination period, the exposure period of the each wavelength band terminating with a second charge sweep signal coinciding with termination of the wavelength illumination period, the second charge sweep signal transferring picked-up image signals from the image pick-up means; and
amplification factor setting means for setting amplification factors in the each wavelength band in the amplification means based on the signals outputted from the image pick-up means after setting the exposure period.

47. The electronic endoscope device according to claim 46 further comprising:
color balance setting designation means for designating balance setting of the colors displayed by the display device, wherein
the exposure period setting means sets the exposure period for the each wavelength band based on the signals outputted by the image pick-up means corresponding to the designation of the color balance setting designation means.

48. The electronic endoscope device according to claim 47, wherein the light source means emits light of a wavelength exciting the object, and the image pick-up means picks up an image of the object by fluorescent light from the object.

49. The electronic endoscope device according to claim 47, wherein the different wavelength bands have a discrete spectral distribution.

50. The electronic endoscope device according to claim 47, wherein at least one exposure period which is set for the each wavelength band is an exposure period obtained by stopping the electronic shutter.

51. The electronic endoscope device according to claim 46, wherein the light source means emits light of a wavelength exciting the object, and the image pick-up means picks up an image of the object by fluorescent light from the object.

52. The electronic endoscope device according to claim 46, wherein the different wavelength bands have a discrete spectral distribution.

53. The electronic endoscope device according to claim 46, wherein at least one exposure period which is set for the each wavelength band is an exposure period obtained by stopping the electronic shutter.

54. The electronic endoscope device according to claim 46, wherein the exposure period setting means sets the exposure period with the electronic shutter for restricting an exposure period set by the rotary optical filter.

55. A color balance adjustment method in an electronic endoscope device for successively illuminating an object with illumination light having different wavelength bands and picking up the images of the object for each wavelength band of this illumination light employed for illumination, comprising the steps of:
picking up the images of the object for each wavelength band based on a prescribed exposure period;
successively supplying illumination light of different wavelength bands using a rotary optical filter, the rotary optical filter being segmented into a plurality of individual wavelength filters defining a wavelength illumination period for each of the different wavelength bands;
setting the exposure period individually for each wavelength band based on the brightness of image signals that correspond to the object image in each wavelength band in response to adjustment coefficients and variably adjusting a generation time of an initial charge sweep signal during each wavelength illumination period for adjusting a staffing point of the exposure period within each wavelength illumination period, the exposure period of the each wavelength band terminating with a second charge sweep signal coinciding with termination of the wavelength illumination period, the second charge sweep signal transferring picked-up image signals;

picking up the images of the object based on the exposure period for each wavelength band that is set;

computing the amplification factor of the image signals for each wavelength band based on the brightness of the image signal corresponded to the object that is picked up based on the exposure period that is set;

adjusting color balance of the object image; and amplifying the image signals for the each wavelength band based on the computed amplification factor.

56. The color balance adjustment method according to claim 55, wherein the exposure period is set with the electronic shutter for restricting an exposure period set by the rotary optical filter.

* * * * *

UNITED STATES PATENT AND TRADEMARK OFFICE
CERTIFICATE OF CORRECTION

PATENT NO.       : 7,670,286 B2
APPLICATION NO.  : 10/869239
DATED            : March 2, 2010
INVENTOR(S)      : Katsuichi Imaizumi et al.

It is certified that error appears in the above-identified patent and that said Letters Patent is hereby corrected as shown below:

Col. 13, line 54: should read;
...Amplification means for amplifying the picked-up image...

Col. 16, line 41: should read;
...period for adjusting a starting point of the...

Signed and Sealed this

Eighteenth Day of May, 2010

David J. Kappos
*Director of the United States Patent and Trademark Office*